United States Patent
Colleran et al.

(10) Patent No.: US 9,101,419 B2
(45) Date of Patent: Aug. 11, 2015

(54) APPARATUS AND METHODS FOR SEPARATING INTERNAL BONE FIXATION DEVICE FROM INTRODUCER

(75) Inventors: Dennis P. Colleran, North Attleboro, MA (US); Robert A. Rabiner, Tiverton, RI (US); Justin G. Dye, Mansfield, MA (US); Narissa Y. Chang, Mansfield, MA (US); Joshua M. Morin, Sturbridge, MA (US)

(73) Assignee: IlluminOss Medical, Inc., East Providence, RI (US)

( * ) Notice: Subject to any disclaimer, the term of this patent is extended or adjusted under 35 U.S.C. 154(b) by 400 days.

(21) Appl. No.: 13/617,327

(22) Filed: Sep. 14, 2012

(65) Prior Publication Data

US 2013/0013009 A1  Jan. 10, 2013

Related U.S. Application Data

(63) Continuation of application No. 12/347,405, filed on Dec. 31, 2008, now Pat. No. 8,777,950.

(60) Provisional application No. 61/019,019, filed on Jan. 4, 2008.

(51) Int. Cl.
| | |
|---|---|
| *A61B 17/72* | (2006.01) |
| *A61B 17/70* | (2006.01) |
| *A61B 17/88* | (2006.01) |
| *A61B 17/29* | (2006.01) |

(52) U.S. Cl.
CPC ......... *A61B 17/7275* (2013.01); *A61B 17/7097* (2013.01); *A61B 17/8863* (2013.01); *A61B 2017/2905* (2013.01)

(58) Field of Classification Search
CPC ................................................. A61B 17/32053
USPC ...................................... 606/174; 30/91.2, 94
See application file for complete search history.

(56) References Cited

U.S. PATENT DOCUMENTS

| | | | |
|---|---|---|---|
| 4,294,251 | A | 10/1981 | Greenwald et al. |
| 4,427,014 | A | 1/1984 | Bel et al. |
| 5,554,111 | A | 9/1996 | Morrey et al. |
| 5,638,827 | A | 6/1997 | Palmer et al. |
| 5,707,374 | A | 1/1998 | Schmidt |

(Continued)

FOREIGN PATENT DOCUMENTS

| | | |
|---|---|---|
| WO | WO 2007/124130 | 11/2007 |
| WO | WO 2008/067214 | 6/2008 |

(Continued)

OTHER PUBLICATIONS

PCT International Search Report based on PCT/US13/049773 dated Oct. 1, 2013.

(Continued)

*Primary Examiner* — David Bates
(74) *Attorney, Agent, or Firm* — Greenberg Traurig, LLP; David J. Dykeman; Roman Fayerberg

(57) ABSTRACT

Apparatus and methods for separating an internal bone fixation device from an introducer are disclosed herein. A device for separating an internal bone fixation device from an introducer includes a functional portion having an outer shaft surrounding and controlling operation of a cutting mechanism; and a control portion having an actuating mechanism for initiating activation of the outer shaft.

20 Claims, 23 Drawing Sheets

(56) References Cited

U.S. PATENT DOCUMENTS

| | | | |
|---|---|---|---|
| 5,718,714 | A | 2/1998 | Livneh |
| 6,053,917 | A | 4/2000 | Sherman et al. |
| 6,358,252 | B1 | 3/2002 | Shapira |
| 6,478,751 | B1 | 11/2002 | Krueger et al. |
| 6,660,006 | B2 | 12/2003 | Markworth et al. |
| 7,341,587 | B2 | 3/2008 | Molz, IV et al. |
| 7,462,182 | B2 | 12/2008 | Lim |
| 7,645,282 | B2 | 1/2010 | Huxel |
| 7,806,900 | B2 | 10/2010 | Rabiner et al. |
| 8,123,757 | B2 | 2/2012 | Zalenski et al. |
| 8,211,121 | B1 | 7/2012 | Quinn et al. |
| 8,777,950 | B2 | 7/2014 | Colleran et al. |
| 2003/0199872 | A1 | 10/2003 | Markworth et al. |
| 2005/0113832 | A1 | 5/2005 | Molz, IV et al. |
| 2005/0143749 | A1 | 6/2005 | Zalenski et al. |
| 2005/0149086 | A1 | 7/2005 | Huxel et al. |
| 2006/0036254 | A1 | 2/2006 | Lim |
| 2006/0241663 | A1 | 10/2006 | Rice et al. |
| 2006/0242839 | A1 * | 11/2006 | Landes et al. ............... 30/90.4 |
| 2008/0039854 | A1 | 2/2008 | Rabiner |
| 2008/0125784 | A1 | 5/2008 | Rabiner |
| 2009/0177204 | A1 | 7/2009 | Colleran et al. |

FOREIGN PATENT DOCUMENTS

| | | |
|---|---|---|
| WO | WO2009088927 | 7/2009 |
| WO | WO2012051312 | 4/2012 |

OTHER PUBLICATIONS

USPTO Office Action in U.S. Appl. No. 12/347,405 mailed Feb. 6, 2014.

PCT International Search Report based on PCT/US2008/088638 dated Feb. 27, 2009.

Extended European Search Report for EP 08869840.2 dated Feb. 8, 2013.

Office Action for U.S. Appl. No. 12/347,405 mailed Oct. 3, 2012.

Office Action for U.S. Appl. No. 12/347,405 mailed Apr. 27, 2012.

* cited by examiner

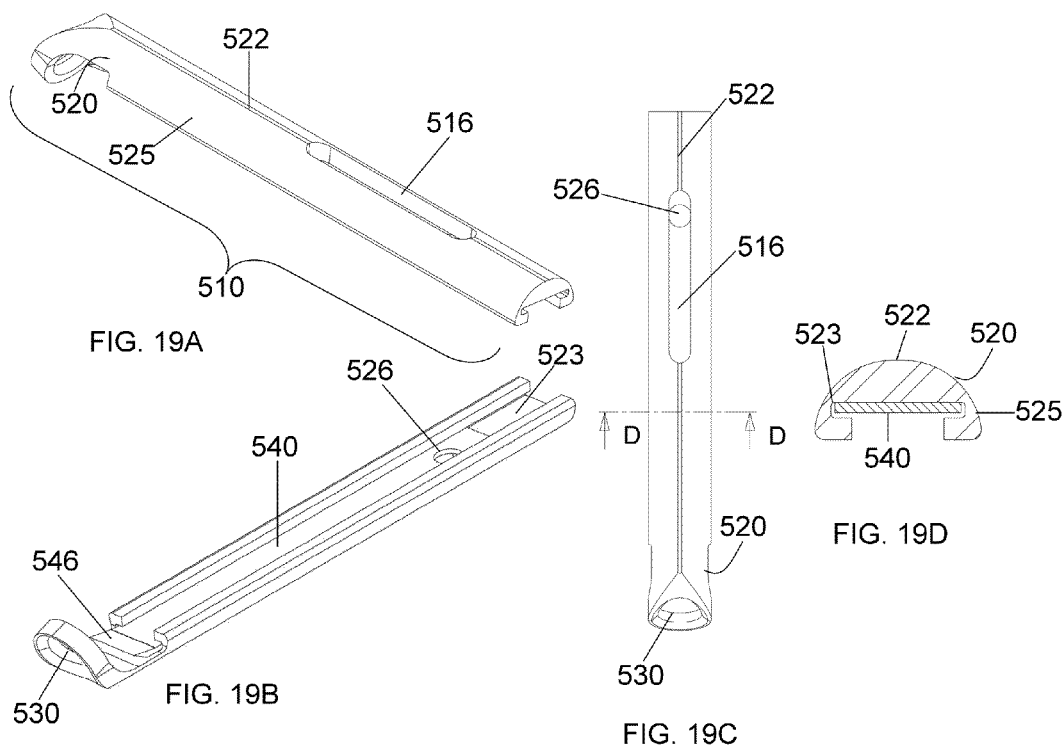

APPARATUS AND METHODS FOR SEPARATING INTERNAL BONE FIXATION DEVICE FROM INTRODUCER

RELATED APPLICATIONS

This application is a continuation of U.S. application Ser. No. 12/347,405, filed Dec. 31, 2008, which claims the benefit of and priority to U.S. Provisional Application Ser. No. 61/019,019, filed Jan. 4, 2008, the entirety of these applications are hereby incorporated herein by reference.

FIELD

The embodiments disclosed herein relate to medical devices for use during an internal bone fixation procedure, and more particularly to cutting devices and methods of using these devices for separating an internal bone fixation device from an introducer.

BACKGROUND

Fracture repair is the process of rejoining and realigning the ends of broken bones. Currently there are several internal approaches to repair, strengthen and support a fractured bone. Conventional internal fixation devices include wires, plates, rods, pins, nails, and screws to support the fractured bone directly, as well as the addition of reinforcing materials to the fractured bone. Newer internal fixation devices include expandable bone fixation devices in which an outer surface of the device contacts the interior surface of the medullary cavity which leads to greater support and strength to the healing bone. For example, one new bone fixation device includes an expandable member that is placed within a cleared-out medullary cavity (void) of the fractured bone in a deflated state. Once in place, the expandable member is expanded from a deflated state to an inflated state by the addition of a reinforcing material from an introducer that is releasably engaged to the expandable member. The reinforcing material is subsequently hardened within the expandable member using a light source. The hardened bone fixation device may then be sealed to enclose the reinforcing material within the bone fixation device and separated from the introducer. The hardened bone fixation device remains within the void of the fractured bone and provides support and proper orientation of the fractured bone resulting in the repair, healing, and strengthening of the fractured bone.

One challenge with the internal bone fixation device is separating the device from the introducer. The edge of the separation should be smooth and not jagged. The force required to separate the device from the introducer should be minimal, thus allowing use by a wide variety of medical professionals.

SUMMARY

Apparatus and methods for separating an internal bone fixation device from an introducer are disclosed herein. According to aspects illustrated herein, there is provided a device for separating an internal bone fixation device from an introducer that includes a functional portion having an outer shaft surrounding and controlling operation of a cutting mechanism; and a control portion having an actuating mechanism for initiating activation of the outer shaft.

According to aspects illustrated herein, there is provided a device for separating an internal bone fixation device from an introducer that includes a functional portion having a cutting mechanism positioned to slide along a bottom surface of a housing, the housing sized and shaped for positioning around the introducer; and a control portion having a connector for engaging the cutting mechanism and an actuating mechanism for initiating activation of the cutting mechanism.

According to aspects illustrated herein, there is provided a method of separating an internal bone fixation device from an introducer that includes providing a cutting device, the cutting device comprising a functional portion having an outer shaft surrounding and controlling operation of a cutting mechanism; and a control portion having an actuating mechanism for initiating activation of the outer shaft; positioning the functional portion of the cutting device over the introducer, wherein the functional portion is positioned so the cutting mechanism is at a junction between the internal bone fixation device and the introducer; activating the actuating mechanism of the control portion, wherein activation of the actuating mechanism translates the outer shaft distally along the cutting mechanism, thereby pushing the cutting mechanism inwards to separate the internal bone fixation device from the introducer; and separating the internal bone fixation device from the introducer.

According to aspects illustrated herein, there is provided a method of separating an internal bone fixation device from an introducer that includes providing a cutting device, the cutting device comprising a functional portion having a cutting mechanism positioned to slide along a bottom surface of a housing, the housing sized and shaped for positioning around the introducer; and a control portion having a connector for engaging the cutting mechanism and an actuating mechanism for initiating activation of the cutting mechanism; positioning the functional portion of the cutting device over the introducer, wherein the functional portion is positioned so the cutting mechanism is at a junction between the internal bone fixation device and the introducer; activating the actuating mechanism of the control portion, wherein activation of the actuating mechanism translates the control portion distally within the opening of the housing, thereby moving the cutting mechanism along the bottom surface of the housing in a distal direction to separate the internal bone fixation device from the introducer; and separating the internal bone fixation device from the introducer.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 3A shows a side view of the functional portion. FIG. 3B shows a sectional view of the functional portion taken along line B-B in FIG. 3A. FIG. 3C shows a partial perspective view of the cutting mechanism alone.

5A shows a side sectional view of the entire device of FIG. 1 in use during an internal bone fixation procedure. FIG. 5B shows a side sectional close-up view of the circled area of FIG. 5A.

FIG. 11A shows an illustrative embodiment of a functional portion having a flexible shaft with a puzzle geometry. FIG. 11B shows an illustrative embodiment of a functional portion having a flexible shaft with a slot geometry.

FIG. 12A shows a side sectional view of the functional portion prior to activation of the flexible device. FIG. 12B shows a side sectional view of the functional portion during activation of the flexible device. FIG. 12C shows a perspective view of the inner flexible shaft and cutting mechanism alone.

FIG. 14A shows a functional portion (partially visible) of the flexible device prior to activation. FIG. 14B shows the functional portion (partially visible) of the flexible device during activation FIG. 14C shows the functional portion (partially visible) of the flexible device after activation, resulting in the separation of the hardened internal bone fixation device from the introducer.

FIG. 17A shows a top perspective view of the device. FIG. 17B shows a bottom perspective view of the device.

FIGS. 19A-D show a functional portion of the device of FIG. 15. FIG. 19A shows a top perspective view of the functional portion. FIG. 19B shows a bottom perspective view of the functional portion. FIG. 19C shows a top plane view of the functional portion. FIG. 19D shows a sectional view of the functional portion taken along line D-D in FIG. 19C.

FIG. 20A shows a functional portion (partially visible) of the device prior to activation. FIG. 20B shows the functional portion after activation, resulting in the separation of the hardened internal bone fixation device from the introducer.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Medical devices and methods for using the devices during an internal bone fixation procedure are disclosed herein. The medical devices disclosed herein are used for separating a hardened internal bone fixation device from an introducer. During an internal bone fixation procedure, a device of the present disclosure is placed over the introducer of an internal bone fixation system and actuated so that a cutting mechanism of the device engages a separation area of the hardened internal bone fixation device and separates the hardened internal bone fixation device from the introducer. Introducers described herein are known to those skilled in the art and include, but are not limited to, delivery catheters, flexible tubes, stents, or any other device that engages an internal bone fixation device and is able to position the internal bone fixation device into a medullary space of a fractured bone.

Figure 1:
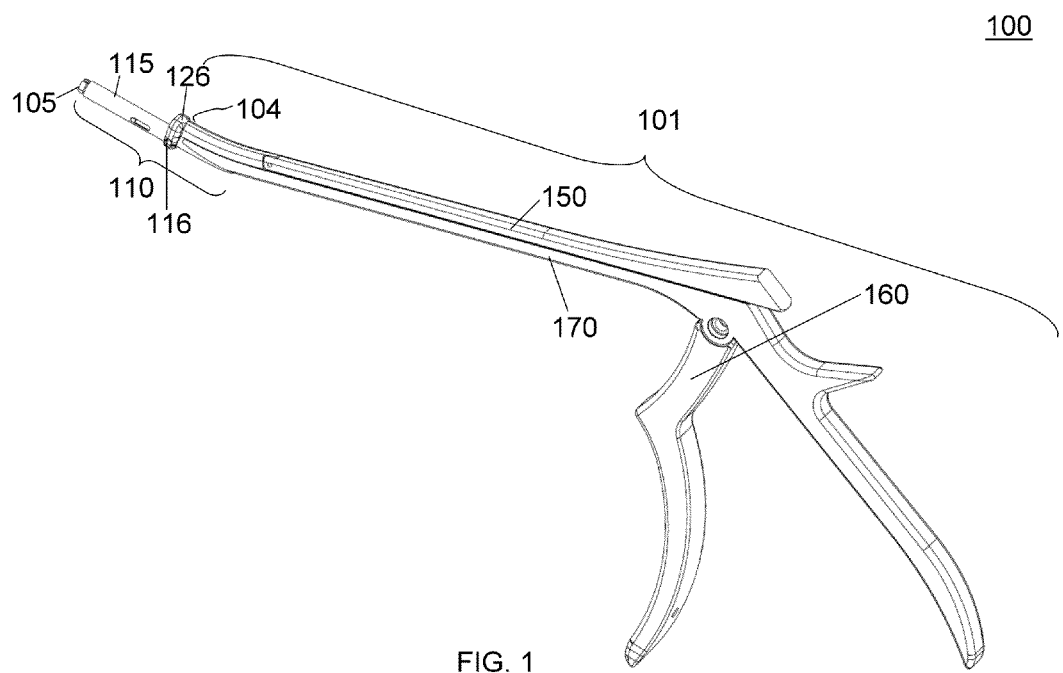
FIG. 1 shows a perspective view of an illustrative embodiment of a device of the present disclosure for the separation of an internal bone fixation device from an introducer.
Figure 2:
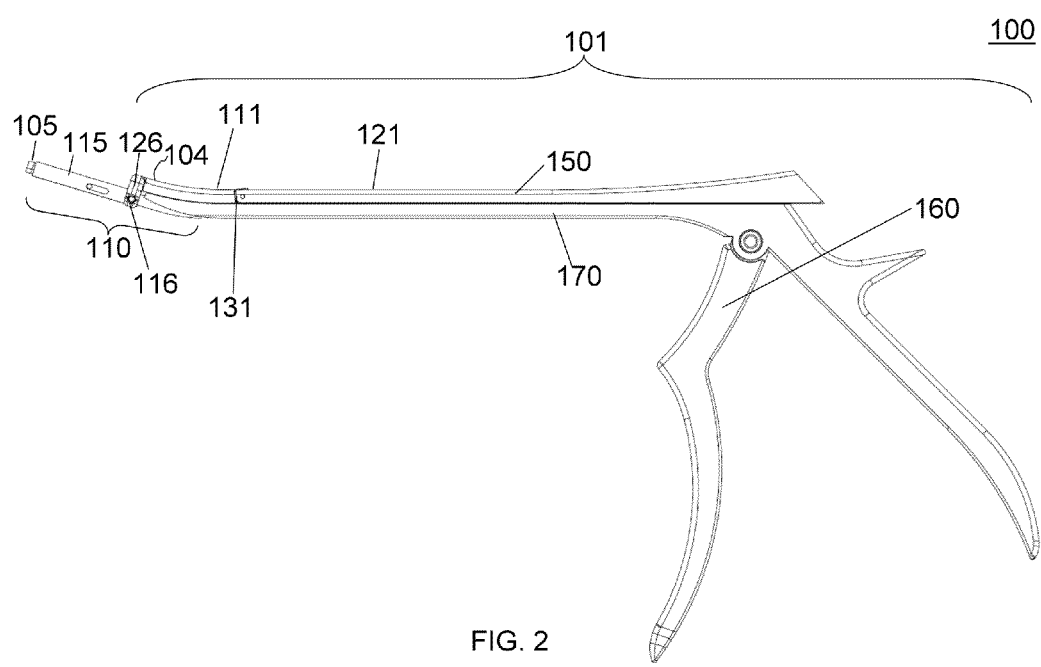
FIG. 2 shows a side view of the device of FIG. 1.
Figure 3:
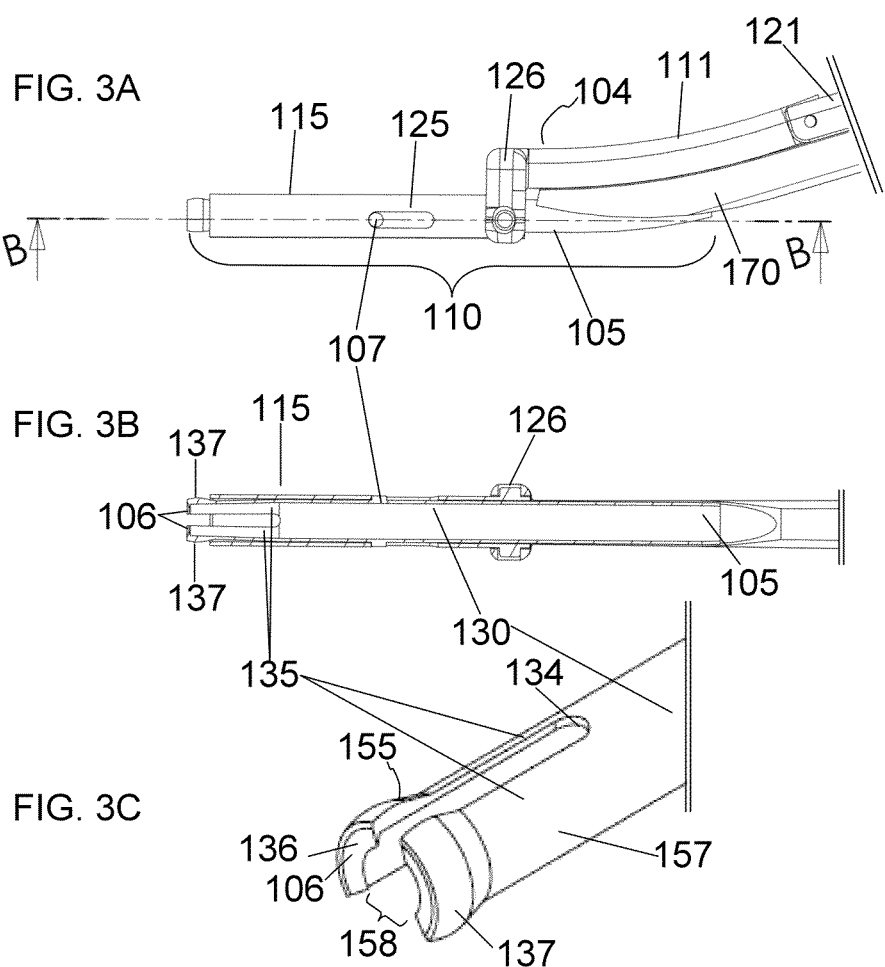
FIGS. 3A-C show close-up views of a functional portion of the device of FIG. 1. The functional portion includes an outer shaft and a cutting mechanism.

An embodiment of a device 100 of the present disclosure for the separation of an internal bone fixation device from an introducer is shown in the various illustrations of FIGS. 1-8. As illustrated in FIGS. 1 and 2, the device 100 includes a control portion 101 having a longitudinal axis, and a functional portion 110 having a longitudinal axis. The functional portion 110 is maintained at a distal end 104 of the control portion 101. A member 126 and associated pins 116 are a functional means of engagement between the control portion 101 and the functional portion 110. The control portion 101 has an upper section 150 and a lower section 170 terminating in a control handle 160. The upper section 150 includes a first section 111 engaging a second section 121, such that the first section 111 can move relative to the second section 121 when the control handle 160 is actuated. Those skilled in the art will recognize that the control portion 101 can include other types of actuating mechanisms, other than a handle, and still be within the scope and spirit of the presently disclosed embodiments. The functional portion 110 includes an outer shaft 115 that surrounds, at least partially, a cutting mechanism 105. The member 126 and the associated pins 116 transfer motion from the first section 111 to the outer shaft 115.

Figure 4:
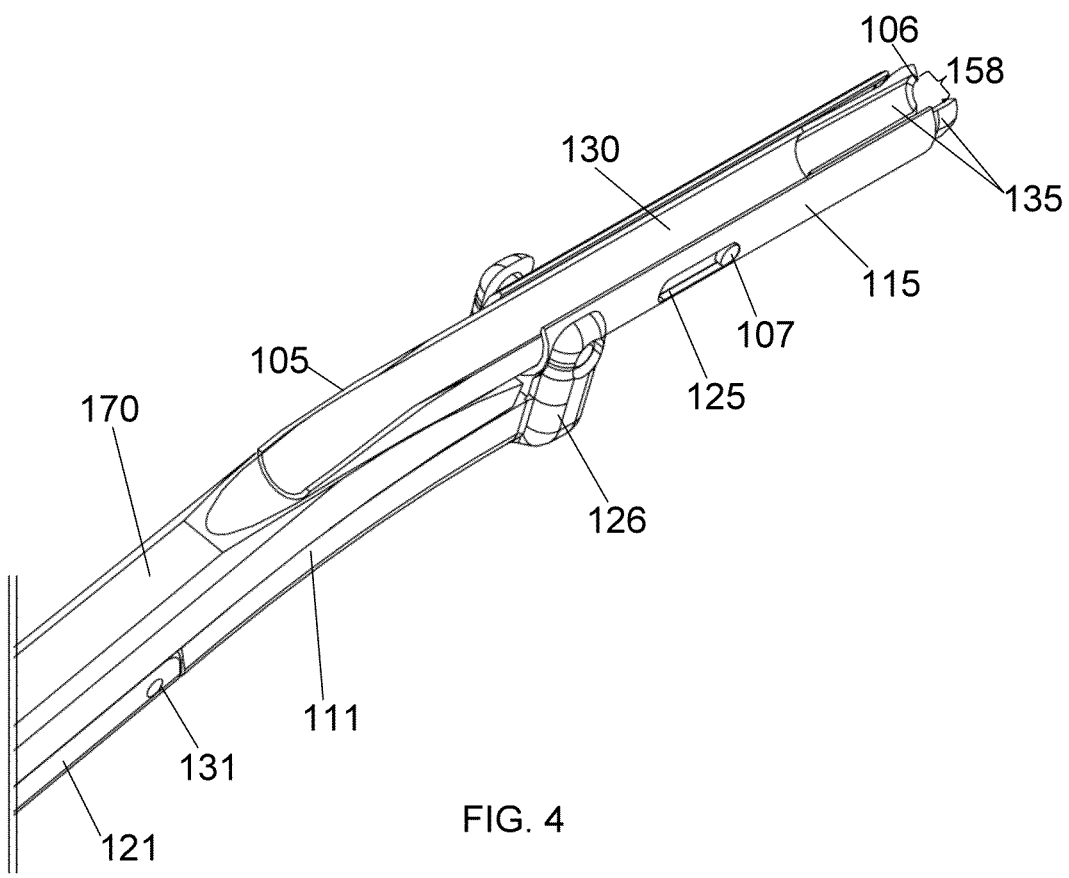
FIG. 4 shows a close-up bottom perspective view of a functional portion of the device of FIG. 1.

FIGS. 3A-B and FIG. 4 show close-up views of the functional portion 110 and the control portion 101 (partial view of the control portion 101). The control portion 101 includes the first section 111 and the second section 121 connected to one another at junction 131. The first section 111 can move relative to the second section 121 during activation of the device 100. The functional portion 110 includes the cutting mechanism 105 that is rigidly affixed to the lower section 170 of the control portion 101 and is at least partially surrounded by the outer shaft 115. The outer shaft 115 is moveably positioned over the cutting mechanism 105, such that a guide or control pin 107 on the cutting mechanism 105 engages with a control slot 125 in a sidewall of the outer shaft 115 to control and direct the motion/operation of the outer shaft 115.

FIG. 3C shows a close-up partial view of the cutting mechanism 105 alone. The cutting mechanism 105 includes a base section 130 that diverges into arm sections 135, the arm sections 135 terminating in a cutting blade 106 on an inner radial surface 136 of each of the arm sections 135. The cutting mechanism 105 has a contoured (i.e., a curved) top surface for receiving the outer shaft 115, and a contoured open bottom surface 158 for positioning over a delivery catheter. The arm sections 135 of the cutting mechanism 105 are separated by a longitudinally oriented slot 134. In an embodiment, one slot 134 creates two arm sections 135. The number of slots 134 can be increased or decreased to achieve the desired number of arm sections 135. The slots 134 are preferentially spaced circumferentially around a distal-most portion 155 of the cutting mechanism 105. These slots 134 impart flexibility to the arm sections 135 such that the distal-most portion 155 of the arm sections 135 are able to compress inward allowing for penetration of the cutting blade 106 into a separation area of a delivery catheter. An outer radial surface 137 at the distal-most portion 155 of the cutting mechanism 105 has a contoured cam shape that is thicker compared to an outer radial surface 157 of the rest of the cutting mechanism 105. During use, the thick outer radial surface 137 of the cutting mechanism 105 engages the outer shaft 115, pushing and squeezing the arm sections 135 towards each other. In an embodiment, the cutting mechanism 105 has a concavo-convex shape, being curved in on a bottom surface and having a more outward curve on a top surface. In an embodiment, the cutting mechanism 105 has a convexo-concave shape, having a top curving edge with one greater bottom curving surface.

FIG. 4 shows a bottom perspective view of the functional portion 110 of the device 100, clearly showing the contoured (i.e., a curved) open bottom surface 158. The outer shaft 115 of the functional portion 110 is contoured to fit on top of the cutting mechanism 105. In an embodiment, the outer shaft 115 surrounds a portion of the cutting mechanism 105. In an embodiment, the outer shaft 115 surrounds the cutting mechanism 105 entirely. In an embodiment, the outer shaft 115 is a rigid shaft. In an embodiment, the outer shaft 115 is a flexible shaft. In an embodiment, the cutting mechanism 105 is composed of a rigid material, and is deficient in or devoid of flexibility. In an embodiment, the cutting mechanism 105 is composed of a flexible material imparting flexibility to the cutting mechanism 105. The cutting mechanism 105 is rigidly affixed to the lower section 170 of the control portion 101.

Figures 5A, 5B:
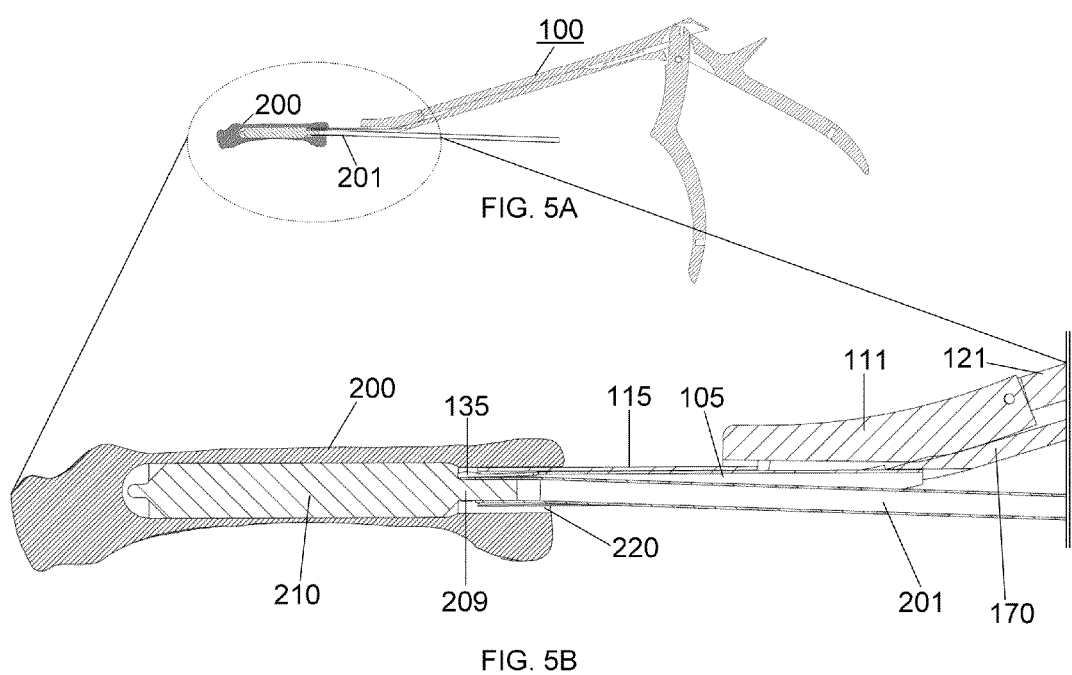
FIGS. 5A-B show side sectional views of the device of FIG. 1 in use during an internal bone fixation procedure. FIG.
Figure 6:
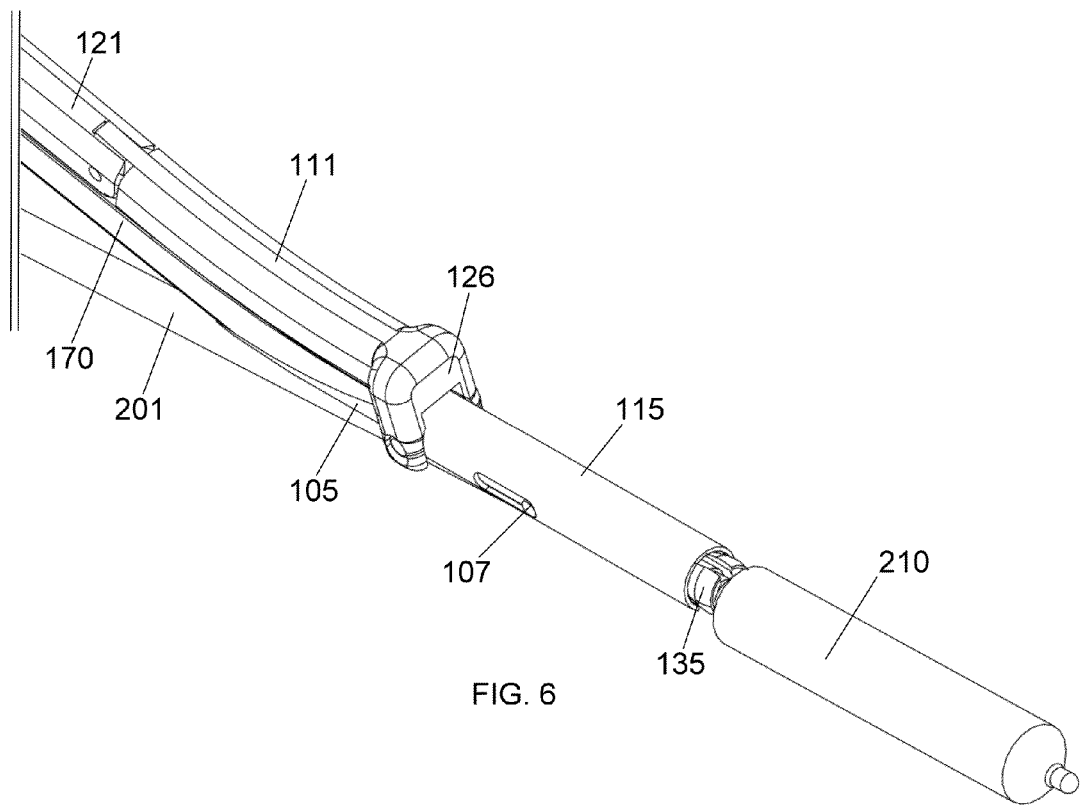
FIG. 6 shows a top perspective view of a functional portion of the device of FIG. 1 in place over a distal end of an introducer of an internal bone fixation system prior to activation of the device.
Figure 7:
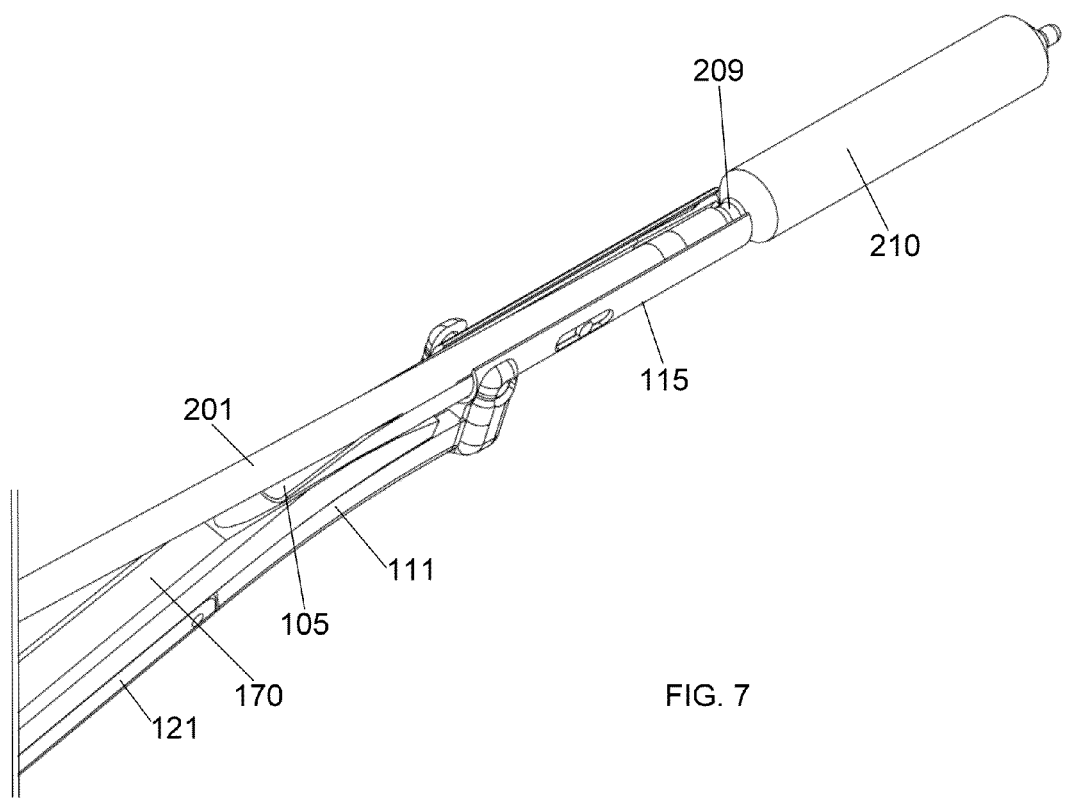
FIG. 7 shows a bottom perspective view of a functional portion of the device of FIG. 1 in place over a distal end of an introducer of an internal bone fixation system during activation of the device.
Figure 8:
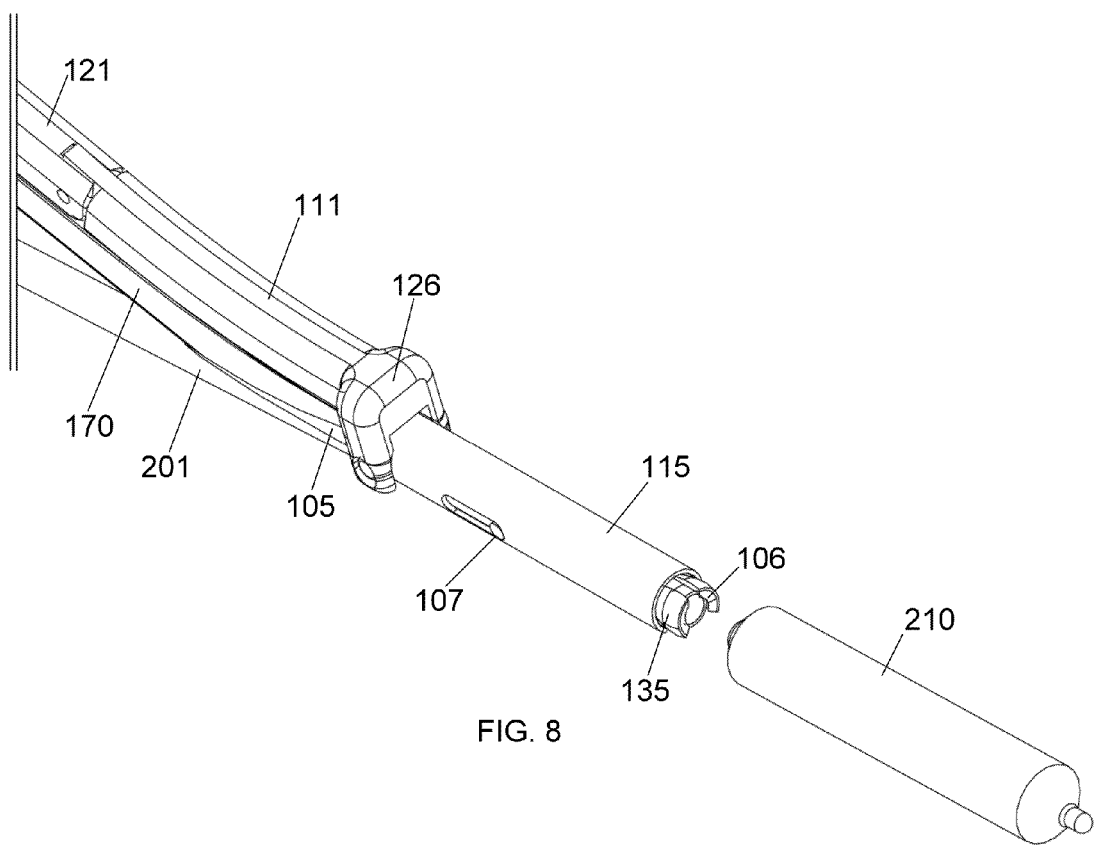
FIG. 8 shows a top perspective view of a functional portion of the device of FIG. 1 in place over a distal end of an introducer of an internal bone fixation system after activation of the device, showing separation of an internal bone fixation device from the introducer.

FIGS. 5A-B in conjunction with FIGS. 6-8, show the device 100 positioned over a delivery catheter 201 of an internal bone fixation system during a procedure for repairing a fractured bone 200. As illustrated in FIGS. 5A-B, the longitudinal axis of the functional portion 110 is positioned over a longitudinal axis of the delivery catheter 201, such that the arm sections 135 of the cutting mechanism 105 surround the delivery catheter 201, as best illustrated in FIGS. 6 and 7. Once the device 100 is activated by squeezing the control handle 160, the outer shaft 115 moves distally along the cutting mechanism 105 guided by the control pins 107 of the cutting mechanism 105 and control slot 125 of the outer shaft 115. The distal movement of the outer shaft 115 results in the outer shaft 115 engaging the thick outer radial surface 137 at the distal-most portion 155 of the cutting mechanism 105. The outer shaft 115 puts pressure on the cutting mechanism 105, squeezing the arm sections 135 towards each other. The cutting blades 106 penetrate at least partially through a separation area 209, making a break/separation in a transverse plane (a plane perpendicular to the longitudinal axis of the functional portion 110 and the delivery catheter 201).

For simplicity, surrounding tissues and bones are not shown in FIGS. 5-8. During a typical procedure, a minimally invasive incision is made through a patient's skin to expose the fractured bone 200. The incision may be made at the proximal end or the distal end of the fractured bone 200 to expose the bone surface. Once the fractured bone 200 is exposed, it may be necessary to retract some muscles and tissues that may be in view of the fractured bone 200. An access hole 220 is formed in the fractured bone 200 by drilling or other methods known in the art. The diameter of the access hole 220 is determined based on the size of the fractured bone 200. The access hole 220 extends through a hard compact outer cortical layer of the fractured bone 200 into the relatively porous inner or cancellous bone. For fractured bones with marrow, medullary material including air, blood, fluids, fat, marrow, tissue and bone debris, should be cleared from the medullary cavity to form a void. The fractured bone 200 may be hollowed out sufficiently to have the medullary material of the medullary cavity up to the cortical bone removed. There are many methods for removing the medullary material that are known in the art and within the spirit and scope on the presently disclosed embodiments including, but not limited to, methods described in U.S. Pat. No. 4,294,251 entitled "Method of Suction Lavage," U.S. Pat. No. 5,554,111 entitled "Bone Cleaning and Drying system," U.S. Pat. No. 5,707,374 entitled "Apparatus for Preparing the Medullary Cavity," U.S. Pat. No. 6,478,751 entitled "Bone Marrow Aspiration Needle," and U.S. Pat. No. 6,358,252 entitled "Apparatus for Extracting Bone Marrow."

A guidewire may be introduced into the fractured bone 2000 via the access hole 220 and placed between various fragments of bone to cross the location of a break within the fractured bone 200. The guidewire may be delivered into the void of the fractured bone and crosses the location of the break so that the guidewire spans multiple sections of bone fragments. An expandable member 210 (internal bone fixation device) of the internal bone fixation system, which is constructed and arranged to accommodate the guidewire, is delivered over the guidewire to the site of the break and spans the bone fragments of the fractured bone 200. Once the expandable member 210 is in place, the guidewire may be removed. The internal bone fixation system is attached to a delivery system which contains a reinforcing material. The reinforcing material is then infused through a void in the delivery catheter 201 and enters the expandable member 210. This addition of the reinforcing material within the expandable member 210 causes the expandable member 210 to inflate. As the expandable member 210 is inflated, the break is reduced. Once orientation of the bone fragments are confirmed to be in a desired position, the reinforcing material within the expandable member 210 may be hardened. The expandable member 210 once hardened, needs to be released from the delivery catheter 201.

The contoured bottom surface of the functional portion 110 of the device 100 is positioned over, or coincidentally with, the delivery catheter 201 of the internal bone fixation system, as best illustrated in FIGS. 6 and 7. The device 100 is then slid through the access hole 220 so that the arm sections 135 of the cutting mechanism 105 surround the separation area 209 located at a junction between a proximal end of the expandable member 210 and a distal end of the delivery catheter 201. FIG. 6 shows a close-up perspective top view of the device 100 over the separation area 209 of the delivery catheter 201 prior to separation. FIG. 7 shows a close-up perspective bottom view of the device 100 over the separation area 209 of the delivery catheter 201 after activation, but prior to separation. To separate the hardened expandable member 210 from the delivery catheter 201, the control handle 160 is squeezed, causing the outer shaft 115 to move distally along the cutting mechanism 105 guided by the control pins 107 of the cutting mechanism 105 and control slot 125 of the outer shaft 115. The distal movement of the outer shaft 115 results in the outer shaft 115 engaging the thick outer radial surface 137 at the distal-most portion 155 of the cutting mechanism 105. The outer shaft 115 puts pressure on the cutting mechanism 105, squeezing the arm sections 135 towards each other. The cutting blades 106 penetrate through the separation area 209, making a break/separation. Further actuation of the control portion 101 causes the distal end of the outer shaft 115 to surpass the distal-most portion 155 of the cutting mechanism 105 which imparts a distally directed longitudinal force on the expandable member 210 further separating the expandable member 210 from the delivery catheter 201. FIG. 8 shows the expandable member 210 separated from the delivery catheter 201.

Figure 9:
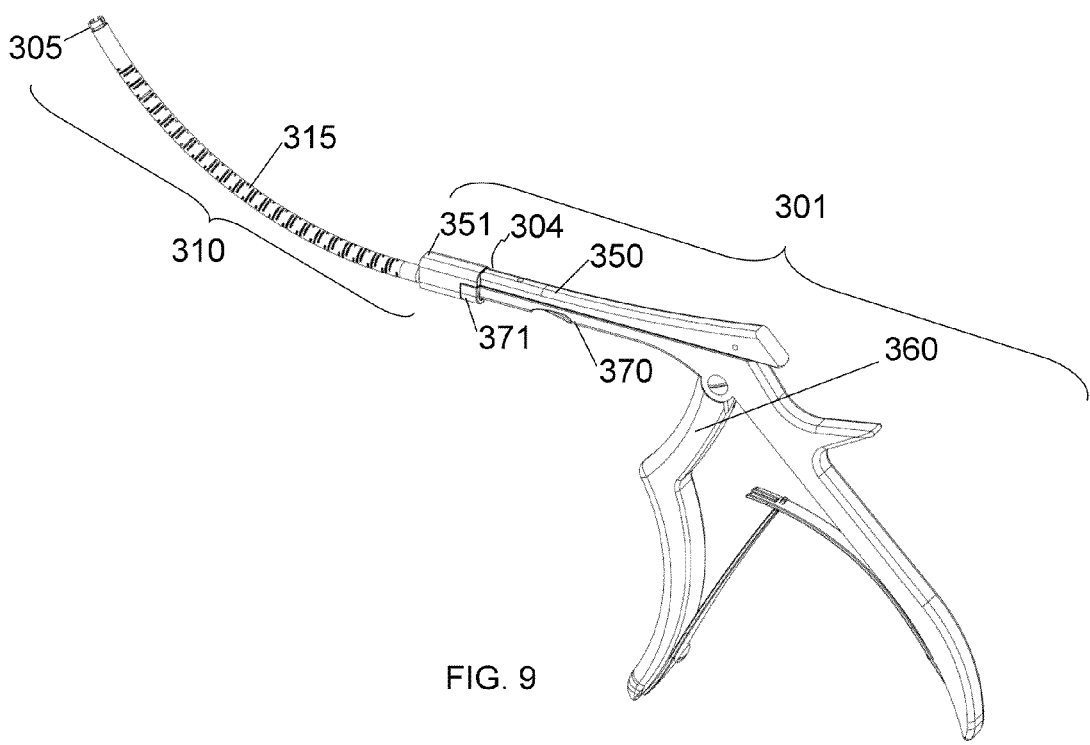
FIG. 9 shows a perspective view of an illustrative embodiment of a flexible device of the present disclosure for the separation of an internal bone fixation device from an introducer.
Figure 10:
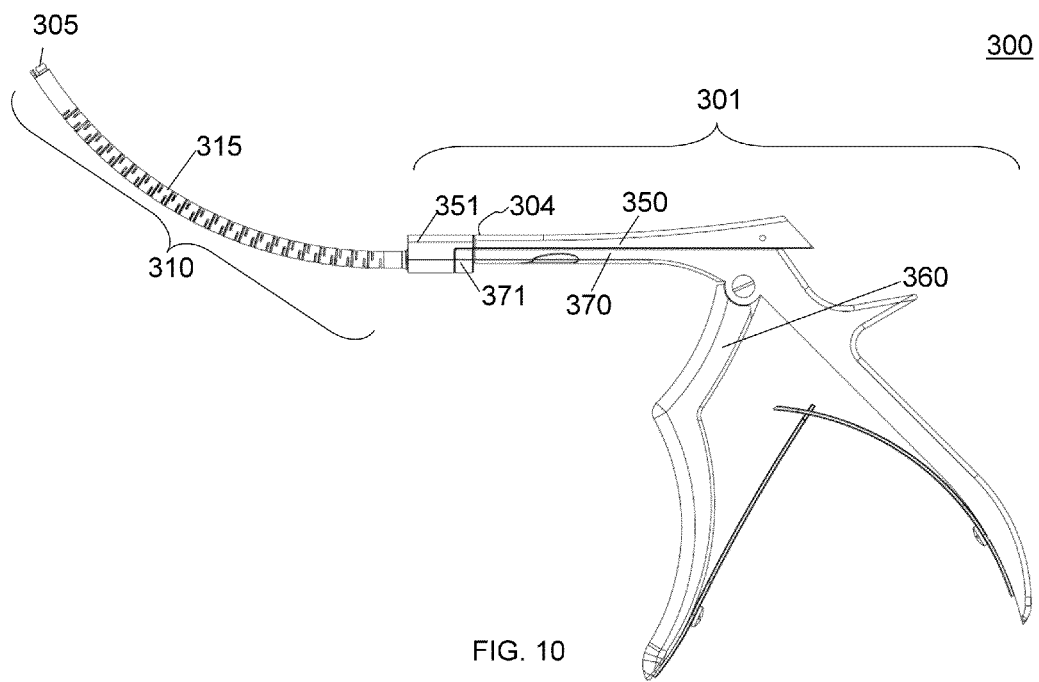
FIG. 10 shows a side view of the flexible device of FIG. 9.

An embodiment of a device 300 of the present disclosure for the separation of an internal bone fixation device from an introducer is shown in the various illustrations of FIGS. 9-14. As illustrated in FIGS. 9 and 10, the device 300 includes a control portion 301, a functional portion 310, and a longitudinal axis therebetween. The control portion 301 has an upper section 350 that terminates at the distal end 304 with a shaft coupling 351 and a lower section 370 also terminating at the distal end 304 with a shaft coupling 371 and having a control handle 360. The functional portion 310 includes an outer flexible moveable shaft 315 surrounding an inner flexible shaft 330 terminating in a cutting mechanism 305. The functional portion 310 is attached to the control portion 301 at distal end 304. In an embodiment, the outer flexible shaft 315 is connected to the upper section 350 of the control portion 301 of the device 300 at the shaft couplings 351 via a threaded connection and the inner flexible shaft 330 is connected to the lower section 370 of the control portion 301 of the device 300 at the shaft coupling 371 via a threaded connection. In an embodiment, the outer flexible shaft 315 can move distally along the inner flexible shaft 330. In an embodiment, both the outer flexible shaft 315 and the inner flexible shaft 330 are made of a metal material that is flexible or has a geometry such that the outer flexible shaft 315 is able to bend and/or flex during use. The outer flexible shaft 315 allows flexibility in multiple planes and can transmit torque and axial force.

Figure 11A:
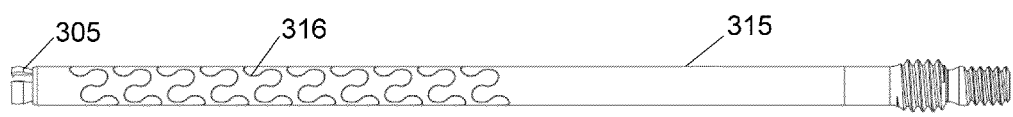
FIGS. 11A-B show side views of two illustrative embodiments of a functional portion of the flexible device of FIG. 9.
Figure 11B:
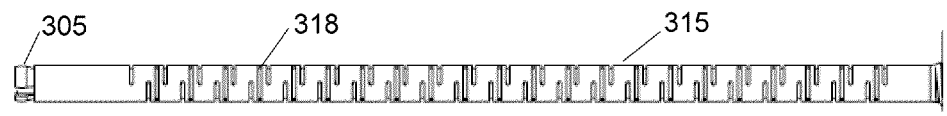

As illustrated in the two embodiments depicted in FIGS. 11A-B, the flexible shaft 315 can have a puzzle geometry (FIG. 11A), a slot geometry (FIG. 11B) or other geometries such that the flexible shaft 315 has flexibility and navigability. As illustrated in FIG. 11A, the puzzle geometry allows flexibility, yet interlocking features 316 increases torque strength and axial stiffness while allowing bending flexibility. In an embodiment, the flexible shaft 315 has a small diameter (for example, about 4 mm to about 5) to minimize trauma and disruption to surrounding soft tissues during use. The flexible shaft 315 has axial strength to avoid buckling and has the ability to transmit an axial force towards the distal end 304. In an embodiment, slots are cut longitudinally along the outer flexible shaft 315 creating gaps that allow for flexibility. In an embodiment, a continuous interlocking shape may be cut longitudinally along the outer flexible shaft 315. In an embodiment, slots are cut longitudinally along the inner flexible shaft 330 creating gaps that allow for flexibility. In an embodiment, a continuous interlocking shape may be cut longitudinally along the inner flexible shaft 330. In both embodiments the gaps and shapes, as well as the orientation and spacing thereof, can vary in order to achieve the desired magnitude and direction of flexibility. In an embodiment, gaps, for example, may be cut using electrical discharge machining, while in another embodiment an interlocking shape, for example, may be cut using laser machining.

Figure 12A:
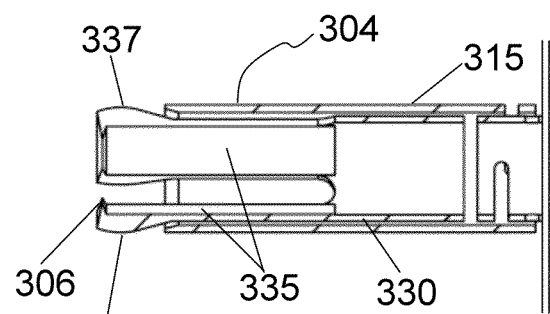
FIGS. 12A-C show close-up views of a functional portion (partially visible) of the flexible device of FIG. 9. The functional portion includes an outer flexible shaft and an inner flexible shaft having a cutting mechanism.
Figure 12B:
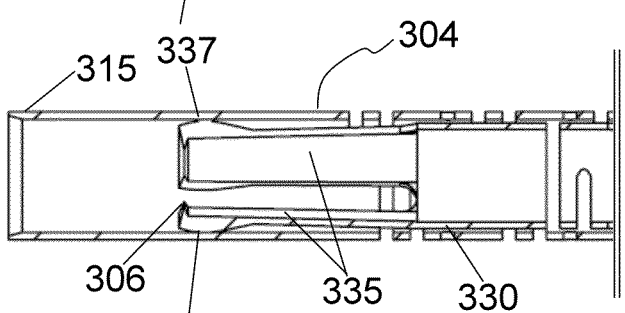
Figure 12C:
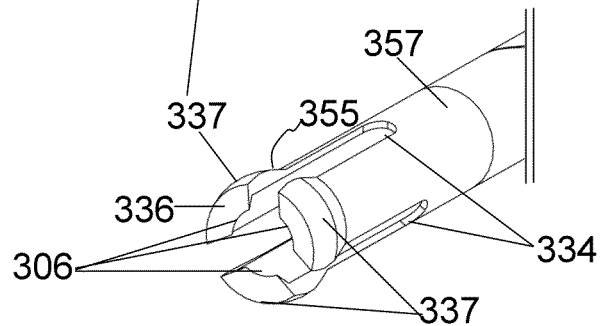

FIGS. 12A-B illustrate close-up side sectional views of the flexible shaft 315 and along with the cutting mechanism 305, prior to activation (FIG. 12A) and after activation (FIG. 12B) of the control handle 360. FIG. 12C shows a close-up partial view of the cutting mechanism 305 alone. The cutting mechanism 305 includes a base section 330 in the form of a flexible shaft that diverges into arm sections 335, the arm sections 335 terminating in a cutting blade 306 on an inner radial surface 336 of each of the arm sections 335. The arm sections 335 of the cutting mechanism 305 are separated by longitudinally oriented slots 334 that are spaced circumferentially around the distal end of the cutting mechanism 305. In an embodiment, three slots 334 create three arm sections 335. The number of slots 334 can be increased or decreased to achieve the desired number of arm sections 335. These slots 334 impart flexibility to the arm sections 335 such that a distal-most portion 355 of the arm sections 335 are able to compress radially inward allowing for penetration of the cutting blade 306 into a separation section of a delivery catheter. An outer radial surface 337 at the distal-most portion 355 of the cutting mechanism 305 has a contoured cam shape that is thicker compared to an outer radial surface 357 of the flexible shaft 330 of the cutting mechanism 305. During use, the thick outer radial surface 337 of the cutting mechanism 305 engages the outer shaft 315, pushing and squeezing the arm sections 335 towards each other. In an embodiment, the cutting mechanism 305 has a concavo-convex shape, being curved in on a bottom surface and having a more outward curve on a top surface. In an embodiment, the cutting mechanism 305 has a convexo-concave shape, having a top curving edge with one greater bottom curving surface. The flexible shaft 315 surrounds a circumference of the cutting mechanism 305. In an embodiment, the cutting mechanism 305 is composed of a flexible material imparting flexibility to the cutting mechanism 305.

Figure 13:
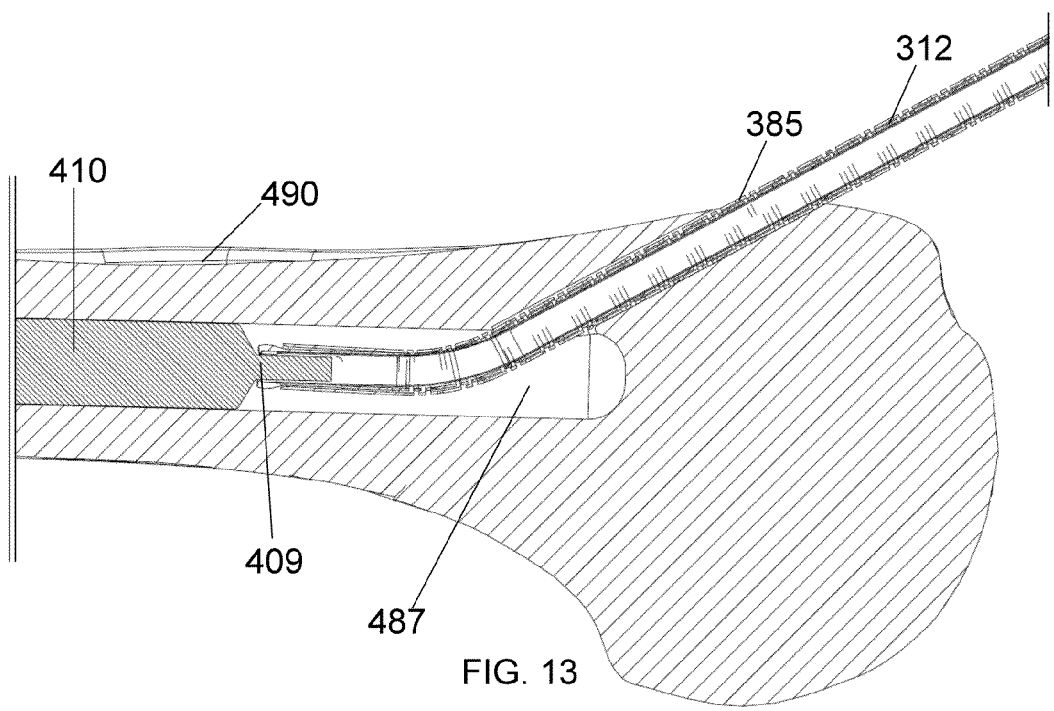
FIG. 13 shows a side sectional view of the flexible device of FIG. 9 in use during an internal bone fixation procedure.
Figure 14A:
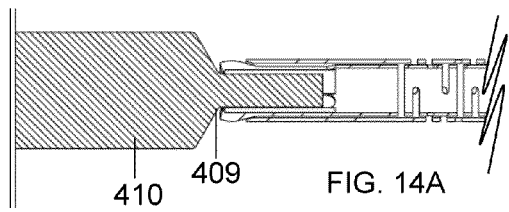
FIGS. 14A-C show side sectional views of an illustrative embodiment of a method for separating a hardened internal bone fixation device from an introducer using the flexible device of FIG. 9.
Figure 14B:
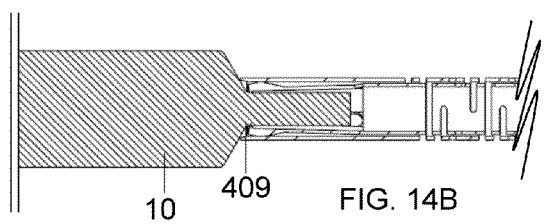
Figure 14C:
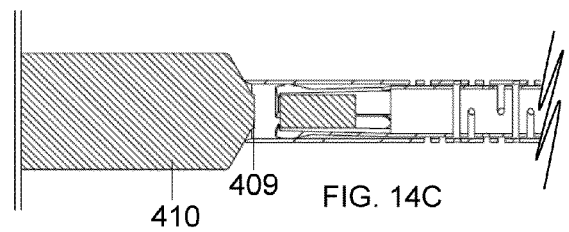

FIGS. 13 and 14 show the device 300 positioned over a delivery catheter (not visible in the figures) of an internal bone fixation system during a procedure for repairing a fractured bone 490. As illustrated in FIGS. 13 and 14A-C, the longitudinal axis of the device 300 is positioned over a longitudinal axis of the delivery catheter, such that the arm sections 335 of the cutting mechanism 305 surround the delivery catheter. Once the device 300 is activated by squeezing the control handle 360, the flexible shaft 315 is translated distally along the inner flexible shaft 330, causing the flexible shaft 315 to engage the thick outer radial surface 337 at the distal-most portion 355 of the cutting mechanism 305. The outer shaft 315 pushes the cutting blades 306 inwards. The cutting blades 306 penetrate at least partially through a separation area 409, making a break/separation in a transverse plane (a plane perpendicular to the longitudinal axis of the device 300 and the delivery catheter).

For simplicity, surrounding tissues and bones are not shown in FIGS. 13 and 14. The initial procedure for reducing a break in the fractured bone 490 is identical to what was described previously for FIGS. 5-8. An expandable member 410 once hardened, needs to be released from the delivery catheter. The flexible shaft 315 of the device 300 engages a proximal end of the delivery catheter, and slides over and down the delivery catheter. The arm sections 335 of the cutting mechanism 305 are placed over the separation area 409 so as to surround the separation area 409. FIG. 14A shows a close-up side sectional view of the flexible shaft 315 over the separation area 409 of the internal bone fixation system prior to separation (bone has been removed for simplicity). The control handle 360 of the device 300 is activated (typically by gripping or squeezing), translating the flexible shaft 315 distally along the inner flexible shaft 330, causing the flexible shaft 315 to engage the thick outer radial surface 337 at the distal-most portion 355 of the cutting mechanism 305. The outer shaft 315 pushes the cutting blades 306 inwards, as illustrated in FIG. 14B. The actuating handle 360 pivots around a pin acting as a lever which causes the top portion 350 of the control portion 301 to slide relative to the lower portion 370 of the control portion 301. In an embodiment, leaf springs between the actuating handle 360 and lower portion 370 act to return the device 300 to its deactivated state. The cutting blades 306 then cut or separate the hardened expandable member 410 from the delivery catheter, as shown in FIG. 14C. Additionally, further actuation of the device 300 causes the outer flexible shaft 315 to surpass the distal end of the cutting mechanism 305 further separating the expandable member from the delivery catheter. The flexible shaft 315 allows for the independent location of the device 300 relative to an internal bone fixation device location and orientation. In use, the device 300 can avoid certain anatomical structures (for example articulating joints, tendon/ligament attachments, etc) to minimize trauma to a patient during a procedure. The flexible shaft 315 can follow the curved shaft of the long bones as most are not perfectly straight.

Figure 15:
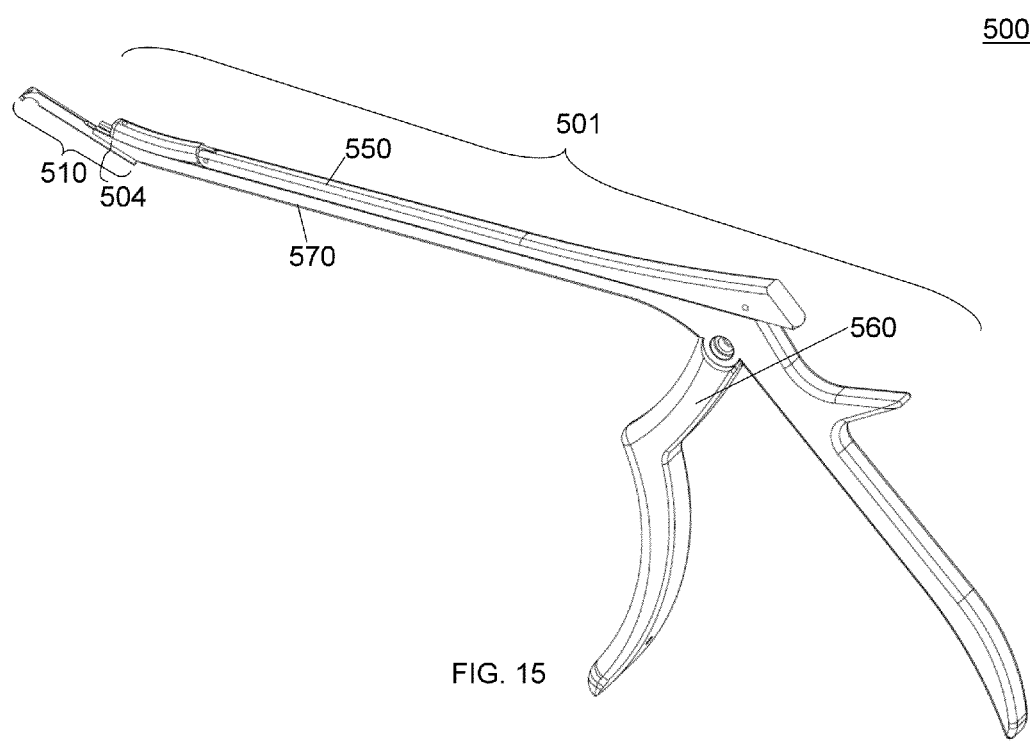
FIG. 15 shows a perspective view of an illustrative embodiment of a device of the present disclosure for the separation of an internal bone fixation device from an introducer.
Figure 16:
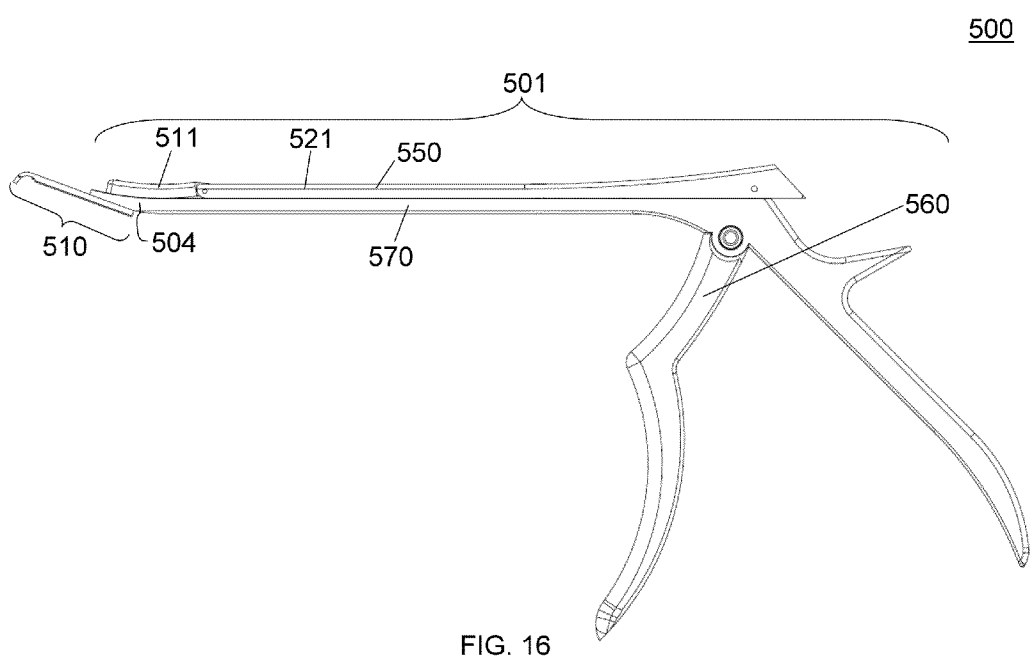
FIG. 16 shows a side view of the device of FIG. 15.

An embodiment of a device 500 of the present disclosure for the separation of an internal bone fixation device from an introducer is shown in the various illustrations of FIGS. 15-20. As illustrated in FIGS. 15 and 16, the device 500 includes a control portion 501 and a functional portion 510 located at a distal end 504 of the control portion 501. The control portion 501 has an upper section 550 and a lower section 570 terminating in a control handle 560. The upper section 550 includes a first section 511 and a second section 521, the first section 511 able to move relative to the second section 521 when the control handle 560 is actuated. The functional portion 510 includes a cutting mechanism 540 (not visible in FIGS. 15 and 16) used to separate an internal bone fixation device from an introducer portion of an internal bone fixation system.

Figure 17A:
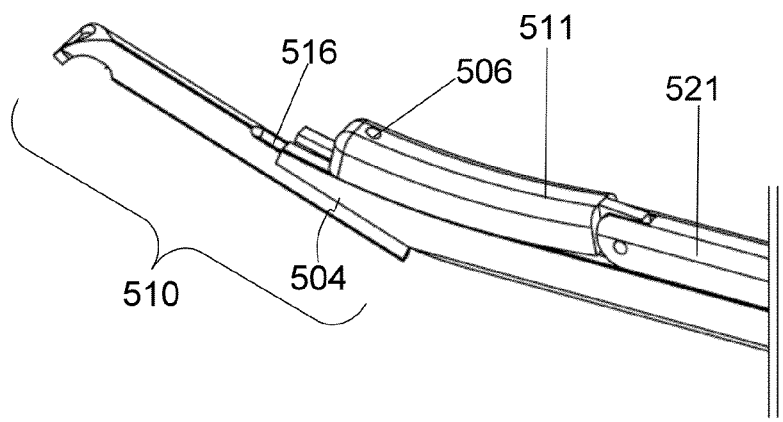
FIGS. 17A-B show close-up perspective views of a functional portion and a control portion (partially visible) of the device of FIG. 15.
Figure 17B:
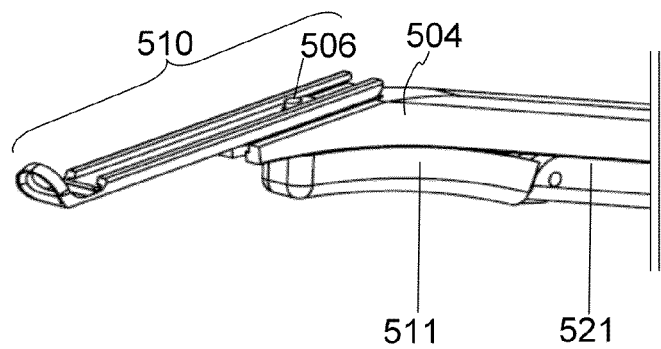
Figure 18:
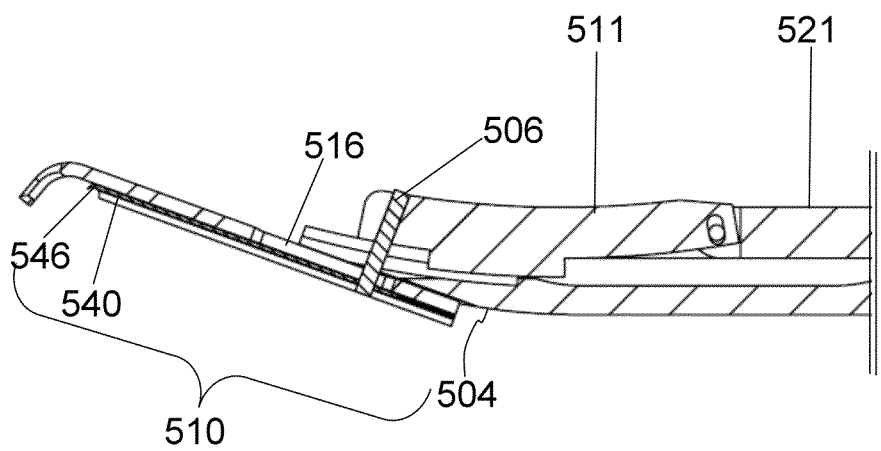
FIG. 18 shows a close-up sectional side view of a functional portion and a control portion (partially visible) of the device of FIG. 15.

FIGS. 17A-B are close-up perspective views of a distal end of the device 500. The first section 511 can move relative to the second section 521, and a connector 506 attaches the first section 511 with the functional portion 510, as best illustrated in FIG. 18. The connector 506 engages the cutting mechanism 540. When the device 500 is actuated, the first section 511 slides along an opening 516 within the functional portion 510, translating linear motion to the cutting mechanism 540. A cutting blade 546 at a tip of the cutting mechanism 540 is similar to a knife or scissor and allows for separation of an internal bone fixation device from a delivery catheter when moved distally in a linear manner.

FIGS. 19A-D show the functional portion 510 of the device 500. FIG. 19A shows a top perspective view of the functional portion 510. FIG. 19B shows a bottom perspective view of the functional portion 510. FIG. 19C shows a top plane view of the functional portion 510. FIG. 19D shows a sectional view of the functional portion 510 taken along line D-D in FIG. 19C. The functional portion 510 includes the cutting mechanism 540 positioned to slide along a bottom surface 523 of a housing 520. The connector 506 engages a hole 526 in the cutting mechanism 540 and moves within an opening 516 in the housing. Since the connector 506 engages the cutting mechanism 540 and the first section 511, when the first section 511 moves distally along the opening 516, the cutting mechanism 540 moves distally along bottom surface 523. The housing 520 includes sidewalls 525 coming down from a top surface 522. An opening 530 at a distal end 514 of the housing 520 can be positioned over an introducer of an internal bone fixation system, as will be described below.

Figure 20A:
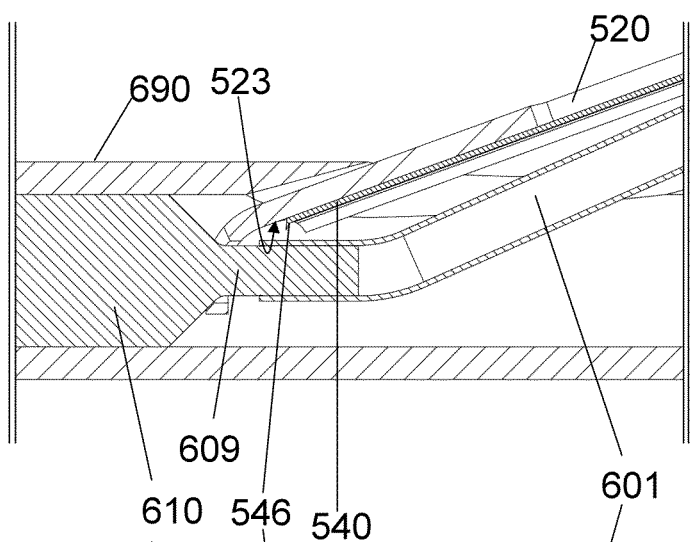
FIGS. 20A-B show side sectional views of an illustrative embodiment of a method for separating a hardened internal bone fixation device from an introducer using the device of FIG. 15.
Figure 20B:
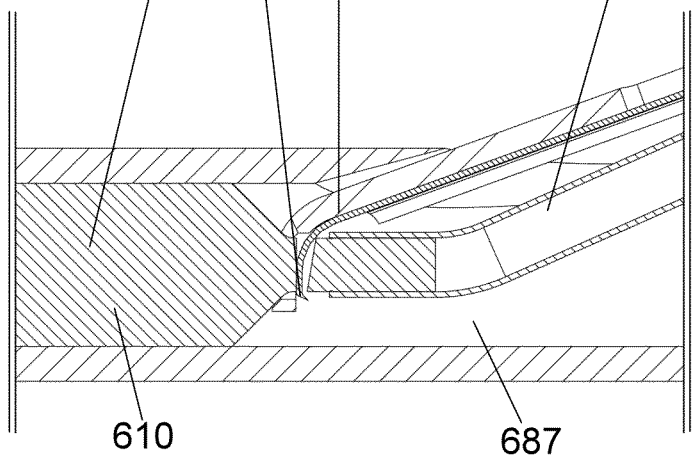

FIGS. 20A-B show the device 500 positioned over a delivery catheter 601 of an internal bone fixation system during a procedure for repairing a fractured bone 690. For simplicity, surrounding tissues and bones are not shown in FIGS. 20A-B. The initial procedure for reducing a break in a fractured bone 690 is identical to what was described previously for FIGS. 5-8. An expandable member 610 once hardened, needs to be released from the delivery catheter 601. The delivery catheter 601 is positioned through the opening 530 of the functional portion 510 of the device 500, and the device 500 is moved down the delivery catheter 601 until the opening 530 is placed at a separation area 609. FIG. 20A shows a close-up side sectional view of the device 500 in place prior to separation. FIG. 20B shows a close-up side sectional view of the device 500 after complete separation. Upon activation of the control handle 560, the cutting mechanism 540 moves along the bottom surface 523 of the housing 520 in a distal direction, pushing the cutting blade 546 through the separation area 609, thus separating the expandable member 610 from the delivery catheter 601.

Figure 21:
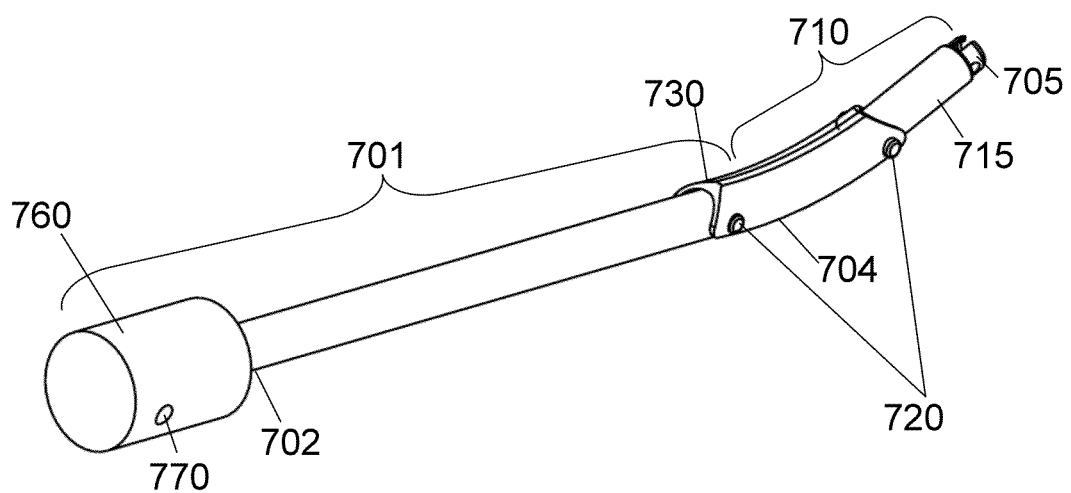
FIG. 21 shows a perspective view of an illustrative embodiment of a device of the present disclosure for the separation of an internal bone fixation device from an introducer.
Figure 22:
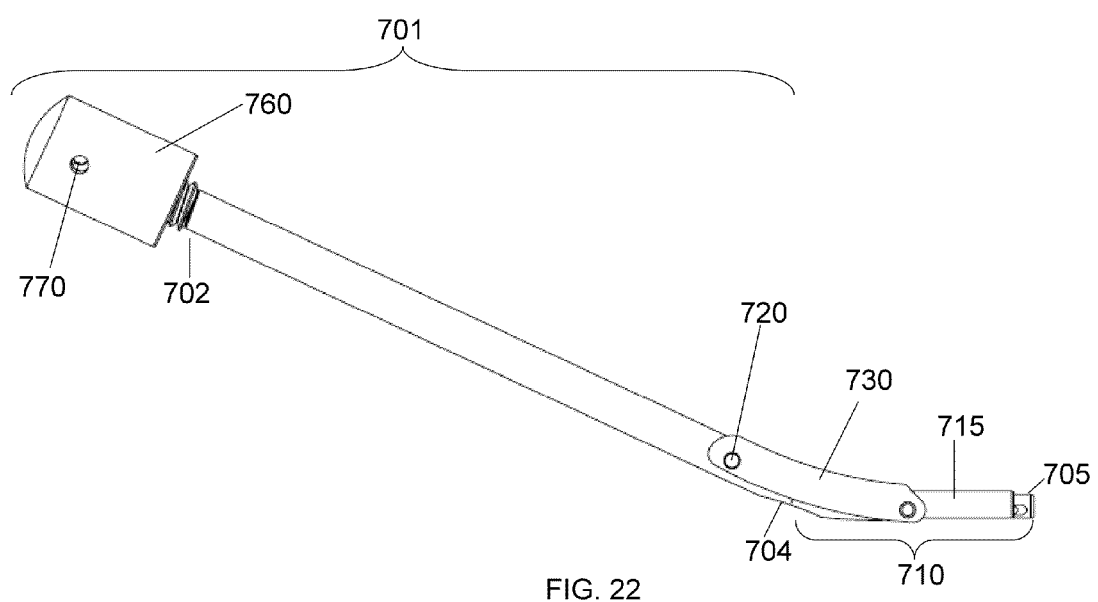
FIG. 22 shows a side view of the device of FIG. 21.
Figure 23:
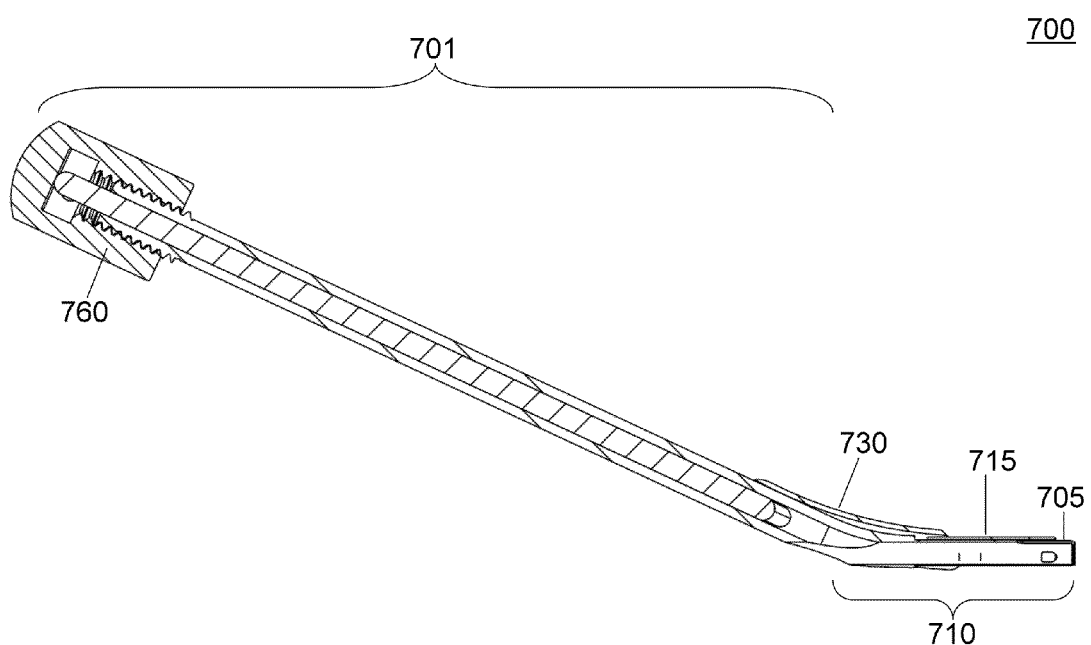
FIG. 23 shows a side sectional view of the device of FIG. 21.

An embodiment of a device 700 of the present disclosure for the separation of an internal bone fixation device from an introducer is shown in the various illustrations of FIGS. 21-23. The device 700 includes an elongated shaft 701 with a proximal end 702, a distal end 704, and a longitudinal axis therebetween. The distal end 704 of the elongated shaft 701 is open at a bottom side such that the device 700 may be placed over an introducer of an internal bone fixation system. The distal end 704 of the device 700 includes at least one cutting arm 705 used to separate an internal bone fixation device from the introducer. In an embodiment, there are two cutting arms 705 at the distal end 704 of the elongated shaft 701. The two cutting arms 705 and the distal end 704 of the elongated shaft 701, are fabricated as a single component. However, those skilled in the art will recognize that the distal end 704 of the elongated shaft 701 and the two cutting arms 705 may be fabricated as two or more separate pieces that are joined together in any manner known to those skilled in the art including welding, adhesives, mechanical fasteners and similar methods. In an embodiment, the elongated shaft 701 is made of a metal material that is flexible or has a spring-type geometry such that the elongated shaft 701 is able to bend and/or flex during use. In an embodiment, the elongated shaft 701 is made from a non-flexible material, such as a stiff stainless steel material. In an embodiment, the distal end 704 of the device 700 is coated with a radiopaque material or contains radiopaque materials that are known to increase radiopacity, which will allow a user to view the distal end 704 of the device 700 using fluoroscopy techniques.

Covering the distal end 704 of the elongated shaft 701 is a clamp tube 710. A link 730 and associated push rods 720 engage the clamp tube 710 to the elongated shaft 701. A knob 760 engages the proximal end 702 of the elongated shaft 701 via pin 770. The entire device 700 has a diameter ranging from about 2 mm to about 4 mm or greater. In an embodiment, the diameter of the device 700 is about 3 mm and is small enough to fit within an access hole of a fractured bone and is flexible enough to conform to the shape of the introducer to which the device 700 is applied.

FIGS. 22 and 23 show side views of the device 700. As seen in FIG. 22, the knob 760 is threaded onto the proximal end 702 of the elongated shaft and is able to translate rotational motion of the elongated shaft 701 into linear motion of the clamp tube 710. FIG. 23 is a cross-sectional side view of the device 700 showing the relationship between the elongated shaft 101, the clamp tube 710, the link 730 and a cutting arm 705. Both the clamp 710 and the link 730 may be fabricated from a rigid material including, but not limited to, a stainless steel or a titanium material. In an embodiment, the clamp 710 is fabricated from a stainless steel material. In an embodiment, the link 730 is fabricated from a stainless steel material. For example, the stainless steel material for the clamp 710 and the link 730 may be a 17-4 stainless steel material.

The clamp tube 710 terminates in a cam portion which engages a ramp section of the cutting arm 705. In an embodiment, the two cutting arms 705 and the distal end 704 of the elongated shaft 701 are all fabricated as a single component. The two cutting arms 705 terminate in a sharp cutting edge. The cutting edge is similar to a knife or scissor and allows for separation of the internal bone fixation device from the introducer when pressure is applied to the cutting edge, as will be described in detail below. The two cutting arms 705 may be constructed of any surgically suitable material. In an embodiment, the two cutting arms 705 are flexible. In an embodiment, the two cutting arms 705 are constructed from a disposable material. In an embodiment, the two cutting arms 705 are constructed from a metal material. In an embodiment, the two cutting arms 705 are constructed from a carbon material or stainless steel material. In an embodiment, the two cutting arms 705 are constructed from stainless steel. For example, the stainless steel material for the two cutting arms 705 may be a 304 stainless steel material. In an embodiment, the two cutting arms 705 are coated with a radiopaque material or contains radiopaque materials that are known to increase radiopacity, which will allow a user to view the device 700 using fluoroscopy techniques.

During a procedure for repairing a fractured bone, the device 700 is positioned over a delivery catheter of an internal bone fixation system. The device 700 is then slid through an access hole provided to access the fractured bone, so that the two cutting arms 705 of the cutting mechanism 705 surround a separation area located at a junction between a proximal end of an expandable member and a distal end of the delivery catheter. If the distal end 704 or the cutting arms 705 are coated with a radiopaque material or contain radiopaque materials that are known to increase radiopacity, a user can view the device 700 using fluoroscopy techniques. To separate the expandable member from the delivery catheter, the knob 760 is rotated, which causes the push rods 720 to translate (push) the link 730. The link 730 in turn translates (pushes) the clamp tube 710. The cam portion of the clamp tube 710 puts pressure on the ramp section of the distal end 704 of the elongated shaft 701. This pressure compresses the cutting edge of the two cutting arms 705 into the expandable member, thereby cutting the expandable member from the delivery catheter.

The devices and methods disclosed herein can be used with an expandable internal bone fixation device. Expandable internal bone fixation devices are known in the art. Examples of expandable internal bone fixation devices that may be used in conjunction with any of the devices disclosed herein include, but are not limited to, those devices described in U.S. patent application Ser. No. 11/789,907 entitled "Apparatus and Method for Delivery of Reinforcing Materials to Bone" and U.S. patent application Ser. No. 11/903,123 entitled "Systems and Methods for Internal Bone Fixation."

Portions of the devices disclosed herein are constructed from surgically suitable materials. In an embodiment, portions of the devices are constructed from disposable materials and intended for single-use applications. In an embodiment, portions of the devices are constructed from metal materials. In an embodiment, portions of the devices are constructed from both disposable and metal materials. In an embodiment, portions of the devices are constructed from carbon containing materials. In an embodiment, portions of the devices are constructed from titanium containing materials. In an embodiment, portions of the devices are constructed from aluminum containing materials. In an embodiment, portions of the devices are constructed from a stainless steel material. Examples of stainless steel materials include, but are not limited to, a 300 series stainless steel and a 600 series stainless steel. In an embodiment, portions of the devices disclosed herein are rigid. In an embodiment, portions of the devices disclosed herein are flexible.

In an embodiment, the cutting mechanisms disclosed herein are fabricated as a single component. In an embodiment, the cutting mechanisms disclosed herein are fabricated as multiple components that are welded, adhered, or fastened together. In an embodiment, portions of the devices disclosed herein can be coated with a radiopaque material or can contain radiopaque materials that are known to increase radiopacity, which will allow a person to view the devices using fluoroscopy techniques. In an embodiment, the devices disclosed herein have a diameter ranging from about 2 mm to about 8 mm. In an embodiment, the devices disclosed herein have a diameter ranging from about 3 mm to about 6 mm. The devices disclosed herein are designed to be small enough to fit within an access hole of a fractured bone.

A method of separating an internal bone fixation device from an introducer includes providing a cutting device, the cutting device comprising a functional portion having an outer shaft surrounding and controlling operation of a cutting mechanism; and a control portion having an actuating mechanism for initiating activation of the outer shaft; positioning the functional portion of the cutting device over the introducer, wherein the functional portion is positioned so the cutting mechanism is at a junction between the internal bone fixation device and the introducer; activating the actuating mechanism of the control portion, wherein activation of the actuating mechanism translates the outer shaft distally along the cutting mechanism, thereby pushing the cutting mechanism inwards to separate the internal bone fixation device from the introducer; and separating the internal bone fixation device from the introducer.

A method of separating an internal bone fixation device from an introducer includes providing a cutting device, the cutting device comprising a functional portion having a cutting mechanism positioned to slide along a bottom surface of a housing, the housing sized and shaped for positioning around the introducer; and a control portion having a connector for engaging the cutting mechanism and an actuating mechanism for initiating activation of the cutting mechanism; positioning the functional portion of the cutting device over the introducer, wherein the functional portion is positioned so the cutting mechanism is at a junction between the internal bone fixation device and the introducer; activating the actuating mechanism of the control portion, wherein activation of the actuating mechanism translates the control portion distally within the opening of the housing, thereby moving the cutting mechanism along the bottom surface of the housing in a distal direction to separate the internal bone fixation device from the introducer; and separating the internal bone fixation device from the introducer.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A device for separating a bone fixation device from an introducer comprising:
    a cutting mechanism having a tubular shape and at a distal end slotted to form flexible arm sections, each flexible arm section having an outer radial surface portion at a distal end;
    a functional portion having an outer shaft surrounding a portion of the cutting mechanism and controlling operation of the cutting mechanism; and
    a control portion having an actuating mechanism for initiating activation of the outer shaft, wherein a distal end of the control portion engages the outer shaft of the functional portion, and
    wherein activation of the actuating mechanism translates the outer shaft to move from a first position distally along the cutting mechanism to a second position over the outer radial surface portions,
        (a) in the first position of the outer shaft, the outer radial surface portions are separated by a first distance;
        (b) in the second position of the outer shaft, the outer radial surface portions are separated by a second distance, wherein the second distance is less than the first distance, to push each flexible arm section of the cutting mechanism toward one another to separate the bone fixation device from the introducer in a void of a bone.

2. The device of claim 1 wherein the outer shaft includes an opening in a sidewall of the outer shaft for engaging the cutting mechanism.

3. The device of claim 1 wherein the cutting mechanism contours at a top surface for receiving the outer shaft and contours at a bottom surface for positioning over the introducer.

4. The device of claim 1 wherein the flexible arm sections includes more than two flexible arm sections.

5. The device of claim 4 wherein the distal end of each arm section has an inner radial surface composed of a cutting blade.

6. The device of claim 1 wherein the flexible arm sections at the distal end of the cutting mechanism are separated by longitudinally oriented slots that are spaced circumferentially around the distal end of the cutting mechanism.

7. The device of claim 4 wherein the base section is composed of a flexible shaft, and the outer shaft is flexible.

8. The device of claim 7 wherein the flexible outer shaft surrounds the flexible shaft of the cutting mechanism.

9. The device of claim 8 wherein a distal end of the control portion engages the flexible outer shaft of the functional portion and the flexible shaft of the cutting mechanism.

10. The device of claim 1 wherein the introducer is from a group consisting of a delivery catheter, a flexible tube, a stent or a device engagable with the bone fixation device that positions the bone fixation device into the void of the fractured bone.

11. The device of claim 1 wherein the functional portion includes the cutting mechanism that is rigidly affixed to a lower section of the control portion and is at least partially surrounded by the outer shaft.

12. The device of claim 1 wherein the outer shaft is moveably positioned over the cutting mechanism, such that a guide or control pin on the cutting mechanism engages with a control slot in a sidewall of the outer shaft to control and direct the operation of the outer shaft.

13. The device of claim 1 wherein the cutting mechanism has a concavo-convex shape, having an inward curve on a bottom surface and having an outward curve on a top surface.

14. The device of claim 1 wherein the cutting mechanism has a convexo-concave shape.

15. A device for separating a bone fixation device from an introducer in a void of a bone, the device comprising:
    a cutting mechanism having a planar shape and a blade at an distal end of the cutting mechanism;
    a functional portion having the cutting mechanism positioned to slide along a bottom surface of a housing, the housing sized and shaped for positioning around the introducer;
    a control portion having a first section attached to a connector for engaging the cutting mechanism; and
    an actuating mechanism for initiating activation of the cutting mechanism for translating the cutting mechanism to linearly move from a first position distally along the bottom surface of the housing to a second position,
        (a) in the first position of the cutting mechanism, the blade is positioned within sidewalls of the housing,
        (b) in the second position of the cutting mechanism, the blade is positioned with a portion of the blade beyond a distal end of the sidewalls of the housing, thereby pushing the portion of the blade to separate the bone fixation device from the introducer in the void of the bone.

16. The device of claim 15 wherein the housing includes a top surface having an opening accepting the connector and allowing movement of the connector within the housing, and a distal end having an opening accepting the introducer and allowing movement of the cutting mechanism along the housing.

17. The device of claim 16 wherein activation of the actuating mechanism translates the control portion distally within the opening of the housing, thereby moving the cutting mechanism along the bottom surface of the housing in a distal direction to separate the bone fixation device from the introducer.

18. The device of claim 15 wherein the housing includes sidewalls coming down from a top surface of the housing, and an opening positioned at the distal end of the housing over the introducer of the internal bone fixation device.

19. The device of claim 15 wherein the control portion has a longitudinal axis and the functional portion has the longitudinal axis, such that the functional portion is maintained at a distal end of the control portion.

20. The device of claim 15 wherein the control portion includes an upper section and a lower section that both terminate in a control handle, such that the upper section includes a first section engaging a second section.

* * * * *